US008776806B2

(12) United States Patent
Hohlbein et al.

(10) Patent No.: US 8,776,806 B2
(45) Date of Patent: Jul. 15, 2014

(54) ORAL HYGIENE DEVICE WITH FLOSS STORAGE CAPABILITY

(75) Inventors: Douglas Hohlbein, Pennington, NJ (US); Alan Sorrentino, Cranbury, NJ (US); James Herbert Kemp, Basking Ridge, NJ (US); Emily Fink, New York, NY (US)

(73) Assignee: Colgate-Palmolive Company, New York, NY (US)

( * ) Notice: Subject to any disclaimer, the term of this patent is extended or adjusted under 35 U.S.C. 154(b) by 435 days.

(21) Appl. No.: 12/142,126

(22) Filed: Jun. 19, 2008

(65) Prior Publication Data

US 2009/0314307 A1   Dec. 24, 2009

(51) Int. Cl.
*A45D 44/18*     (2006.01)
*A46B 11/00*     (2006.01)

(52) U.S. Cl.
USPC ............................................ 132/309; 132/311

(58) Field of Classification Search
USPC ......... 132/309, 308, 310, 311, 313, 314, 315, 132/321–329; 15/167.1; 206/851, 823
See application file for complete search history.

(56) References Cited

U.S. PATENT DOCUMENTS

| 901,835 | A | * | 10/1908 | Ringer | 401/123 |
|---|---|---|---|---|---|
| 1,473,766 | A | * | 11/1923 | Healy | 132/309 |
| 1,658,221 | A | | 2/1928 | Brown | |
| 1,738,389 | A | | 12/1929 | Cunningham | |
| 1,792,429 | A | | 2/1931 | Klinger | |
| 1,813,360 | A | | 7/1931 | Priest | |
| 1,847,495 | A | * | 3/1932 | Priest | 132/309 |
| 2,837,098 | A | * | 6/1958 | Sorboro | 132/324 |
| 3,782,397 | A | | 1/1974 | McCord | |
| 3,847,168 | A | | 11/1974 | Schlegel | |
| 3,853,134 | A | | 12/1974 | McCord | |
| 3,861,406 | A | | 1/1975 | Stitt | |
| 3,890,986 | A | | 6/1975 | Gerlich | |
| 3,939,853 | A | | 2/1976 | Spanondis | |
| 4,294,269 | A | * | 10/1981 | Kyte | 132/309 |
| 4,403,625 | A | * | 9/1983 | Sanders et al. | 132/323 |
| 4,865,481 | A | | 9/1989 | Scales | |
| 4,887,621 | A | | 12/1989 | Vallieres | |
| 4,911,187 | A | * | 3/1990 | Castillo | 132/321 |
| 4,919,156 | A | * | 4/1990 | Gipson | 132/309 |
| 4,957,125 | A | | 9/1990 | Yaneza | |
| 4,987,910 | A | | 1/1991 | Lowe | |
| D316,782 | S | | 5/1991 | Torbenson | |
| 5,040,553 | A | | 8/1991 | Londonoet et al. | |
| 5,044,386 | A | * | 9/1991 | Nelson | 132/309 |
| 5,097,852 | A | | 3/1992 | Wu | |

(Continued)

FOREIGN PATENT DOCUMENTS

CN    2678595 Y    2/2005
CN    101001552 A    7/2007

(Continued)

*Primary Examiner* — Robyn Doan
(74) *Attorney, Agent, or Firm* — Ryan M. Flandro

(57) ABSTRACT

An oral hygiene device is provided having a head and a handle. The handle is configured to accommodate a user's hand grip when the head is inserted into a user's mouth. The head is further configured to accommodate, at a distal end of the handle, a proximal end of the head. One of the head and the handle is provided with a cavity configured to receive a supply of floss. The cavity becomes accessible when the head and the handle are at least partially detached from one another.

21 Claims, 5 Drawing Sheets

(56) References Cited

U.S. PATENT DOCUMENTS

| | | | |
|---|---|---|---|
| D336,782 S | | 6/1993 | Vela et al. |
| 5,348,028 A | | 9/1994 | Gustavel |
| 5,365,956 A | | 11/1994 | Guadiana |
| 5,415,187 A | | 5/1995 | Heneveld |
| 5,423,427 A | | 6/1995 | Brown |
| D362,341 S | | 9/1995 | Sprague |
| 5,490,530 A | | 2/1996 | Snowden |
| 5,676,167 A | | 10/1997 | Garner |
| 5,769,553 A | | 6/1998 | Chaudhri et al. |
| D397,554 S | | 9/1998 | Sprague |
| D402,812 S | | 12/1998 | Goff |
| D407,224 S | | 3/1999 | Wilson et al. |
| 5,875,510 A | * | 3/1999 | Lamond et al. ............ 15/167.1 |
| 5,906,213 A | * | 5/1999 | Diffendal .................. 132/309 |
| 5,924,429 A | * | 7/1999 | Morando .................. 132/309 |
| 5,950,641 A | | 9/1999 | Taveras |
| 6,009,886 A | | 1/2000 | Labranche et al. |
| 6,095,157 A | * | 8/2000 | Brown ....................... 132/309 |
| 6,105,587 A | | 8/2000 | Dunn |
| 6,390,103 B1 | | 5/2002 | Manso |
| 6,526,991 B2 | | 3/2003 | Bodwalk |
| D481,870 S | | 11/2003 | Bochner |
| 6,672,783 B1 | | 1/2004 | Licata et al. |
| 6,766,807 B2 | | 7/2004 | Piccolo et al. |
| 6,772,770 B1 | | 8/2004 | Williams, Sr. |
| D516,317 S | | 3/2006 | Wong |
| 7,124,894 B1 | | 10/2006 | Dobos |
| 7,198,051 B1 | | 4/2007 | Festa |
| 7,201,172 B2 | | 4/2007 | Nanda |
| 7,234,473 B1 | | 6/2007 | Winters |
| 7,237,560 B2 | * | 7/2007 | Macias et al. ............ 132/309 |
| 2002/0100490 A1 | | 8/2002 | Bodwalk |
| 2003/0005544 A1 | | 1/2003 | Felix |
| 2003/0019503 A1 | | 1/2003 | Foster |
| 2003/0188761 A1 | | 10/2003 | Garcia et al. |
| 2004/0040571 A1 | | 3/2004 | Williams, Sr. et al. |
| 2004/0134510 A1 | | 7/2004 | van Vilsteren et al. |
| 2004/0237995 A1 | | 12/2004 | Mualem et al. |
| 2005/0211262 A1 | | 9/2005 | Raab |
| 2006/0048790 A1 | | 3/2006 | Petner |
| 2006/0070636 A1 | * | 4/2006 | Peters, Jr. ................ 132/324 |
| 2006/0086369 A1 | | 4/2006 | Wilkinson |
| 2006/0260635 A1 | | 11/2006 | Dabney |

FOREIGN PATENT DOCUMENTS

| | | |
|---|---|---|
| DE | 20019627 U1 * | 4/2001 |
| RU | 2077872 | 4/1997 |
| TW | 253135 | 8/1995 |

* cited by examiner

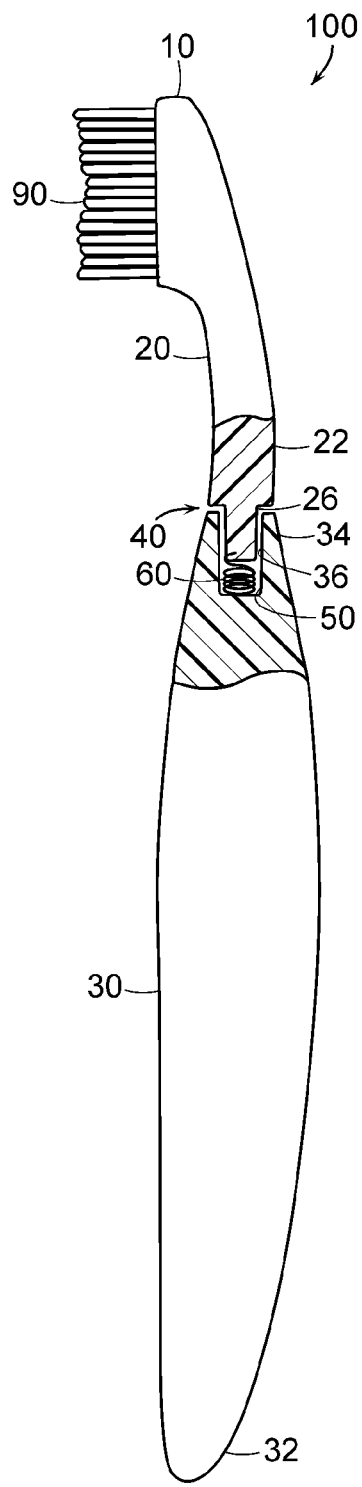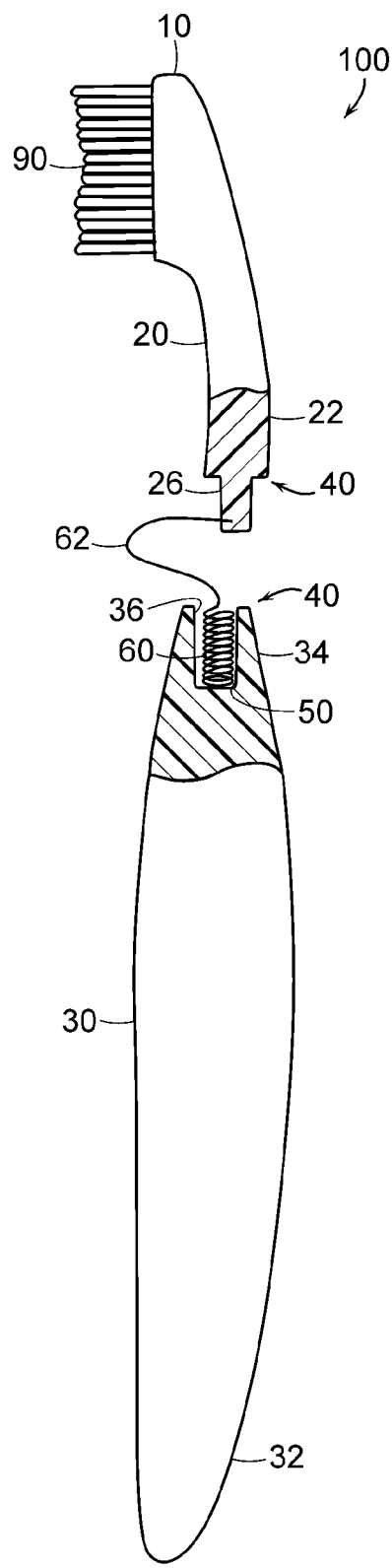
FIG. 1
FIG. 2

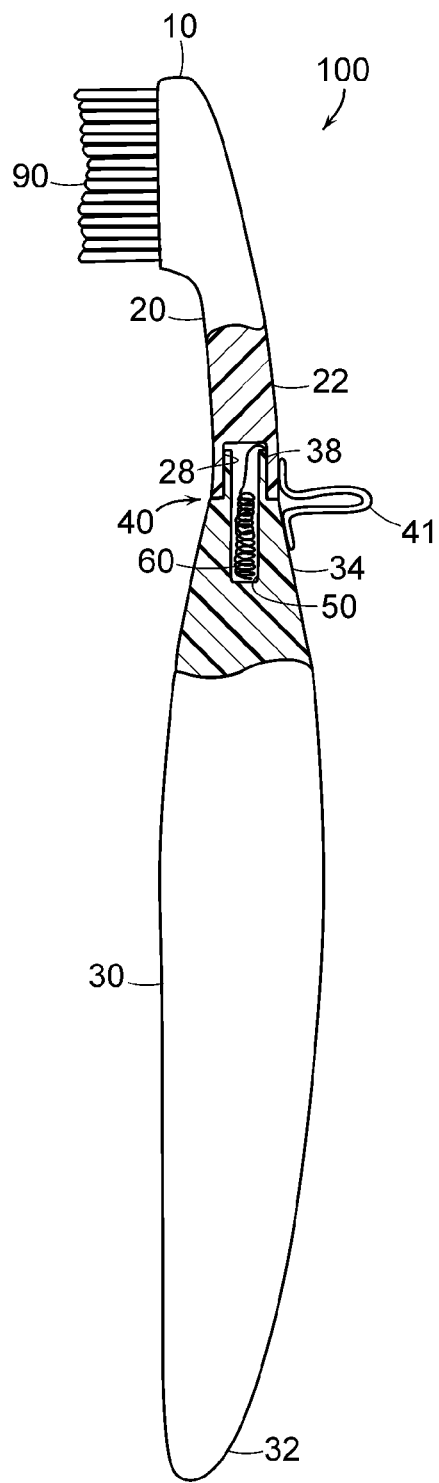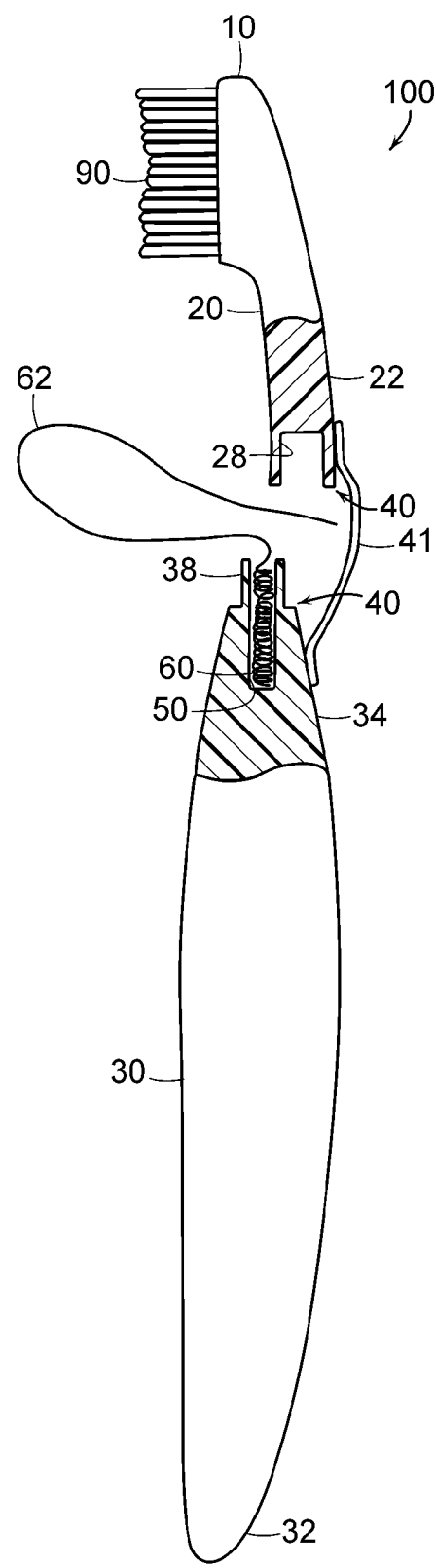
FIG. 5
FIG. 6 ular to a oral hygiene device having an engagement interface between a head and a handle, with the supply of floss being accessible from the interface.

US 8,776,806 B2

ORAL HYGIENE DEVICE WITH FLOSS STORAGE CAPABILITY

BACKGROUND OF THE INVENTION

This invention relates generally to an oral hygiene device configured to store a supply of floss, and in particular, to a oral hygiene device having an engagement interface between a head and a handle, with the supply of floss being accessible from the interface.

Oral hygiene devices, such as toothbrushes, inter-dental devices, gum massagers, tongue scrapers, etc. are known for promoting oral hygiene. The use of floss to provide another level of oral hygiene care is also known. Certain products have combined oral hygiene devices with floss storage capabilities. However, these products are generally cumbersome with respect to a user accessing and using the floss. For example, certain products store a supply of floss in relatively bulky external housings in the grip area of a toothbrush handle, such that the user's grip on the handle of the toothbrush is less than optimal during the toothbrushing process. Other products store a supply of floss in housings at the base of the toothbrush handle such that accessing the floss requires changing one's grip on the handle. Even further, with some products, water used to rinse the toothbrush could enter the area where the floss is stored, thereby ruining and contaminating the stored floss. This negatively impacts the ability of the user to easily rinse the toothbrush.

Providing a simple and convenient device for both promoting oral hygiene and flossing and that reduces or overcomes some or all of the difficulties inherent in prior known devices would be desirable. Particular objects and advantages will be apparent to those skilled in the art, that is, those who are knowledgeable or experienced in this field of technology, in view of the following disclosure of the invention and detailed description of certain embodiments.

BRIEF SUMMARY OF THE INVENTION

Certain embodiments of an oral hygiene device, which can provide improved access to a supply of floss and ease of flossing, are described.

In accordance with a first aspect, an oral hygiene device has a head and a handle. The handle is configured to accommodate a user's hand grip when the head is inserted into a user's mouth. The handle is further configured to accommodate, at a distal end of the handle, a proximal end of the head. One of the head and the handle is provided with a cavity configured to receive a supply of floss. The cavity becomes accessible when the head and the handle are at least partially detached from one another.

The oral hygiene device may include a supply of floss received within the cavity. A strand of the supply of floss may be affixed to the handle or the head or to both the handle and the head.

According to another aspect, a method for using an oral hygiene device is provided. The oral hygiene device includes a head for insertion into a user's mouth during an oral hygiene session and a handle for accommodating a hand grip of a user during an oral hygiene session. The method includes at least partially disconnecting the head from the handle at an interface area and accessing a supply of floss from the interface area. The method may further include cutting a portion of the supply of floss from the oral hygiene device.

According to even another aspect, a toothbrush includes a head having bristles and a handle removably engaged to the head at an interface. The handle defines a cavity having an opening at the interface. The cavity is configured to accommodate a supply of floss.

Features and advantages disclosed here will be further understood from the following detailed disclosure of certain embodiments.

BRIEF DESCRIPTION OF THE DRAWINGS

FIG. 1 is a partial section view of an oral hygiene device, in a first configuration.

FIG. 2 is a partial section view of an oral hygiene device, in a second configuration, according to the embodiment of FIG. 1.

FIG. 5 is a partial section view of even another embodiment of an oral hygiene device, in a first configuration.

FIG. 6 is a partial section view of an oral hygiene device, in a second configuration, according to the embodiment of FIG. 5.

Figure 3:
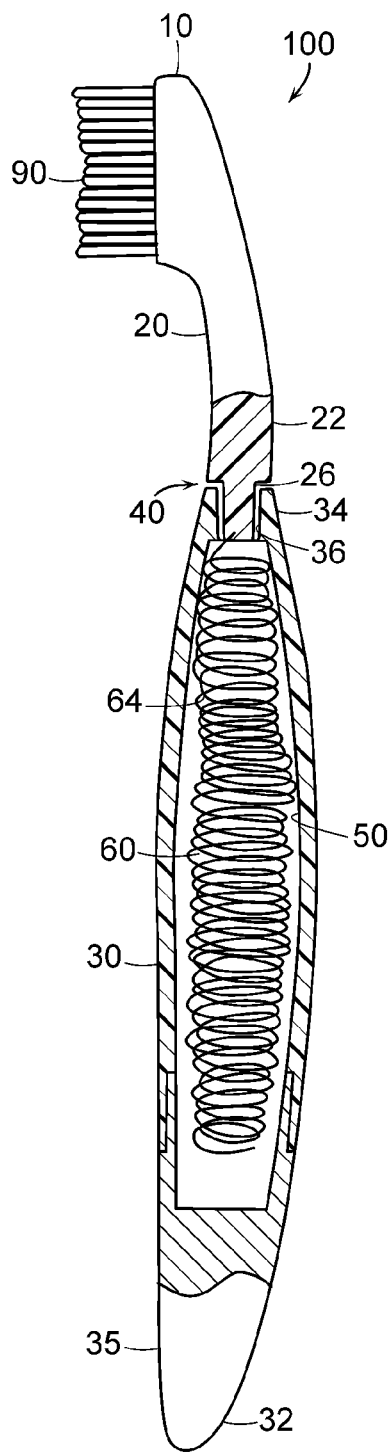
FIG. 3 is a partial section view of another embodiment of an oral hygiene device, in a first configuration.

The figures referred to above are not drawn necessarily to scale and should be understood to provide a representation of an oral hygiene device, illustrative of the principles involved. Some features of the oral hygiene device depicted in the drawings may have been enlarged or distorted relative to others to facilitate explanation and understanding. The same reference numbers are used in the drawings for similar or identical components and features shown in various alternative embodiments. An oral hygiene device as disclosed herein would have configurations and components determined, in part, by the intended application and environment in which they are used.

DETAILED DESCRIPTION OF THE INVENTION

An oral hygiene device may be embodied in various forms. One embodiment of an oral hygiene device 100 is shown in FIG. 1. In the embodiment of FIG. 1, oral hygiene device is a toothbrush 10. Oral hygiene device 100 includes a head 20. Head 20 is configured for insertion into a user's mouth for purposes of oral hygiene. In the embodiment of FIG. 1, head 20 is a toothbrush head. Oral hygiene device further includes a handle 30 having a proximal end 32 and a distal end 34.

Head 20 is engaged to handle 30 at interface 40. Interface 40 is provided below the portion of oral hygiene device 100 that is generally insertable into a user's mouth and above the portion of oral hygiene device 100 that generally provides a hand grip portion during an oral hygiene session. Specifically, interface 40 is provided between the distal end 34 of handle 30 and a proximal end 22 of head 20. As best shown in FIG. 2, head 20 is detachable from handle 30, thereby providing, among other things, the capability of replacing handle 30 or head 20 or of storing oral hygiene device 100 in a compact form.

Oral hygiene device 100 also includes a supply of floss 60. The supply of floss 60 is accessible when the head 20 and the handle 30 are at least partially disconnected.

Handle 30 is configured to accommodate a user's grip during an oral hygiene session. In order to provide sufficient grasping capability, handle 30 will generally be at least approximately 2 inches long. More typically, handle 30 may be from approximately 3 inches to approximately 5 inches long. For disposable or travel oral hygiene devices, it is expected that the handle length would be at the lower end of this range. For example, a disposable toothbrush may have a handle length of from approximately 2.5 inches to approximately 4.0 inches. In this regard, handle 30 may be ergonomically designed to provide improved grip and comfort.

As shown in FIGS. 1 and 2, distal end 34 of handle 30 includes a bore 36 configured for engagement with a shaft 26 at proximal end 22 of head 20. Bore 36 may have any suitable cross section, including, by way of non-limiting examples, circular, square, triangular, oval or even non regular. Shaft 26 of head 20 may have a cross section that complements the cross section of bore 36. Shaft 26 may have a different cross sectional shape than that of bore 36 but still be insertable into bore 36.

Shaft 26 may be slid ably or rotatably insertable into bore 36. In one embodiment, shaft 26 may have a slight interference fit with bore 36, such that a slight tug by a user is necessary to detach head 20 from handle 30.

As shown in the embodiment of FIG. 1, handle 30 includes in interior cavity 50. Interior cavity 50 communicates with bore 36 and is configured to receive a supply of floss 60.

In one embodiment, the supply of floss 60 includes a single use strand 62. Such a single use strand 62 would be particularly applicable for a disposable oral hygiene device. The single use strand could be from approximately one-half to 24 inches long. A length of from approximately 12 to 22 inches may be appropriate for most users. A length of approximately 1½ feet may be particularly suitable.

As shown in FIG. 2, single use strand 62 may be affixed or gripped at one end to handle 30. Also as best shown in FIG. 2, strand 62 may be affixed or gripped at its other end to head 20. Thus, when head 20 is detached from handle 30, strand 62 may extend between head 20 and handle 30. When strand 62 is gripped or affixed at one end (either to handle 30 or head 20), a suitable length of the strand may be less by up to approximately 9 inches. When strand 62 is gripped or affixed at both ends, a suitable length of the strand may be even less. As an example, a length of from approximately one-half inch to approximately 6 inches may be particularly suitable when the strand is gripped or affixed by both the handle and the head. For purposes of this disclosure, any extension of a supply of floss between head 20 or handle 30 is not considered to "attach" head 20 to handle 30.

Figure 4:
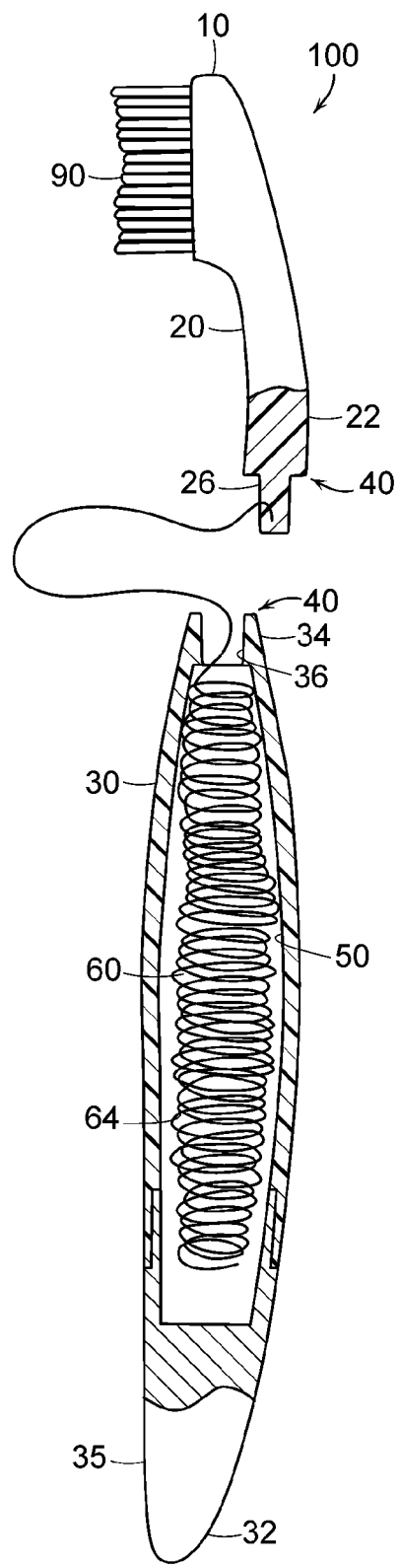
FIG. 4 is a partial section view of an oral hygiene device, in a second configuration, according to the embodiment of FIG. 3.

In one embodiment, handle 30 is a molded as a single unit. In another embodiment, handle 30 may be composed of two or more pieces subsequently permanently assembled. In even another embodiment, handle 30 may be composed of two or more pieces that are detachably coupled to one another. By way of non-limiting example and referring to FIGS. 3 and 4, handle 30 could be provided with an end cap 35. End cap 35 may snap, thread or be press-fit onto the main body of handle 30. When end cap 35 is removed, interior cavity 50 could be accessible from the end of handle 30 such that the supply of floss 60 could be inserted into interior cavity 50. FIG. 4 illustrates an embodiment wherein end cap 35 forms a proximal end of handle 30, such that upon removal of end cap 35, interior cavity 50 is accessible from the proximal end of handle 30.

In another embodiment, strand 62 is affixed to handle 20, but not to head 20. Thus, referring to FIGS. 5 and 6, when head 20 is detached from handle 20, strand 62 remains affixed to handle 30 at one end, but the other end of strand 62 is free. Alternatively, strand 62 may be affixed to head 20, but not to handle 30.

Figure 10:
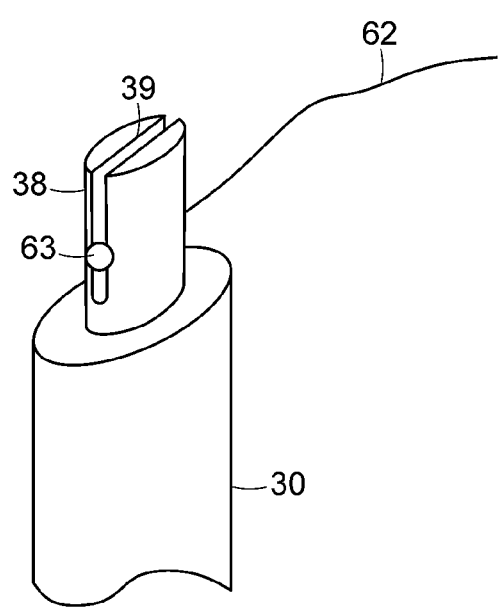
FIG. 10 is a perspective view of an affixment of a strand of floss to a distal end of a handle.
Figure 11:
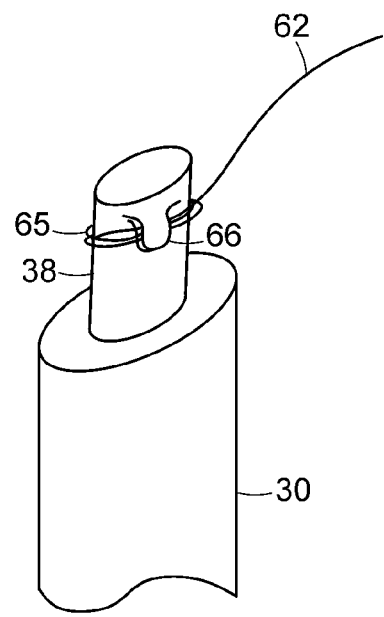
FIG. 11 is a perspective view of an alternative affixment of a strand of floss to a distal end of a handle.

In even another embodiment, strand 62 is initially affixed to one or both of head 20 and handle 30, but may be easily unfastened, if desired by the user, from its affixment to head 20 and/or handle 30. By way of non-limiting example and referring to FIG. 10, such a detachable affixment of the floss to the handle or head could be accomplished by knotting 63 (or otherwise enlarging or looping) the end of the strand and inserting the strand into a slot 39 or under a hook that captures the enlarged or looped end. As another example and referring to FIG. 11, an end of floss strand 62 could be frictionally engaged with handle 30 via multiple windings 65 of floss around a portion of handle 30. A projection or flap 66, under which the strand could be slid, could further be provided to assist in affixing the strand to the head or handle. Other methods for detachably affixing the floss to the head or handle will become readily apparent to those skilled in the art, given the benefit of this disclosure. The ability to unfasten the strand from one or both of the head or the handle may facilitate use of the floss by the user.

As even another alternative embodiment, as shown in FIGS. 5 and 6, the proximal end of head 20 may include a bore 28 and the distal end 34 of handle 30 may include a shaft 38. Shaft 38 is configured for insertion into bore 28 of head 20. Further, an interior chamber 50 may be provided within shaft 38 and/or generally within handle 30. Other suitable configurations and arrangements of shafts and bores on the head and the handle will become readily apparent to those skilled in the art, given the benefit of this disclosure.

In the embodiment of FIGS. 5 and 6, head 20 is partially disconnectable or detachable from handle 30. For example, as illustrated in FIGS. 5 and 6, a hinge or strap 41 may connect head 20 to handle 30. Strap 41 may be of any length and may, optionally, be detachable from one or both of head 20 and handle 30, as may be desired by a user.

Figure 7:
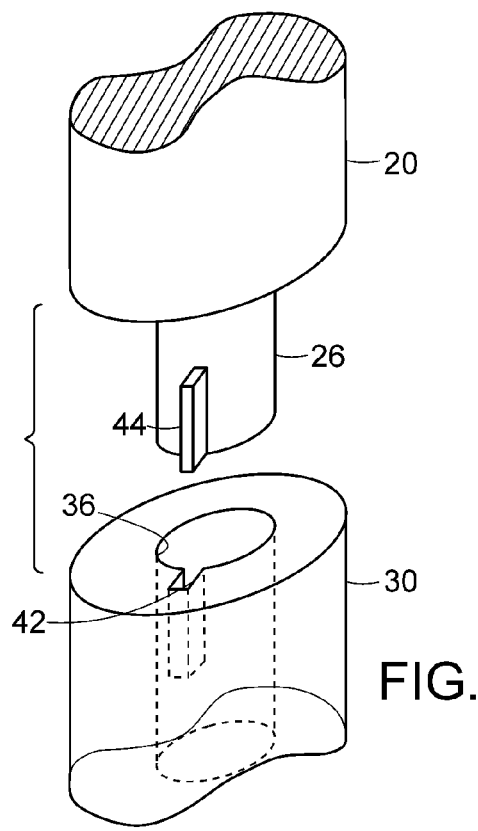
FIG. 7 is a perspective view of an embodiment of an interface between a head and a handle.

Interface 40 may further include a keyway 42 for complementary engagement with a key 44. As shown in FIG. 7, keyway 42 may be located on handle 30 and the key 44 may be located on head 20. Alternatively, head 20 may include the keyway for complementary engagement with a key on handle 30. Suitable configurations for a keyway and a key will become readily apparent to those skilled in the art, given the benefit of this disclosure. Key 44 and keyway 42 may be used to orient head 20 relative to handle 30 and to prevent relative rotational motion from occurring between handle 20 and head 30 when oral hygiene device 100 is being used.

Figure 8:
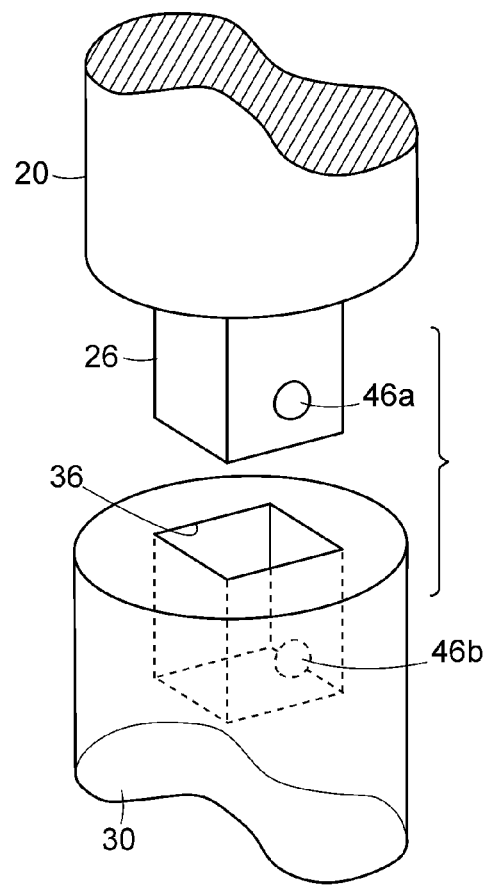
FIG. 8 is a perspective view of an alternative interface between a head and a handle.

In one embodiment, one or both of shaft 26 and bore 36 may include an engagement element 46. Referring to FIG. 8, engagement element 46a may be, by way of non-limiting example, an elastomeric bump or detent. A complementary engagement hollow or dimple 46b may be provided on the other of shaft 26 and bore 36. Engagement elements 46a, 46b assist in keeping head 20 engaged with handle 30.

Figure 9:
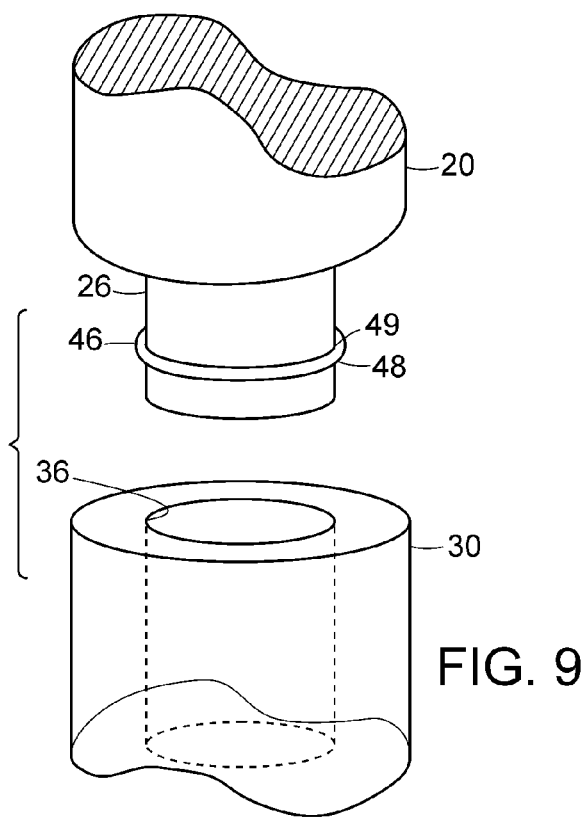
FIG. 9 is a perspective view of another alternative interface between a head and a handle.

Alternatively, as shown in FIG. 9, in one embodiment, engagement element 46 may include a seal member 48 provided in a channel 49. Seal member 48 and channel 49 may be provided within on shaft 26 as shown (or alternatively, within bore 36 (not shown)). In this embodiment, seal member 48 may both assist in keeping head 20 engaged with handle 30 and in keeping fluid from penetrating into an interior cavity of handle 30.

Referring back to FIGS. 3 and 4, in one embodiment the supply of floss 60 may include a longer strand 64, suitable for providing several flossing sessions. For example, a disposable oral hygiene device may be suitable for multiple uses (such as would be contemplated by a traveler away from home for several days). In such case, having a supply of floss readily available for the entire trip may be desired. Strand 64 may be wound on a spool, freely coiled or otherwise arranged within interior cavity 50.

Figure 12:
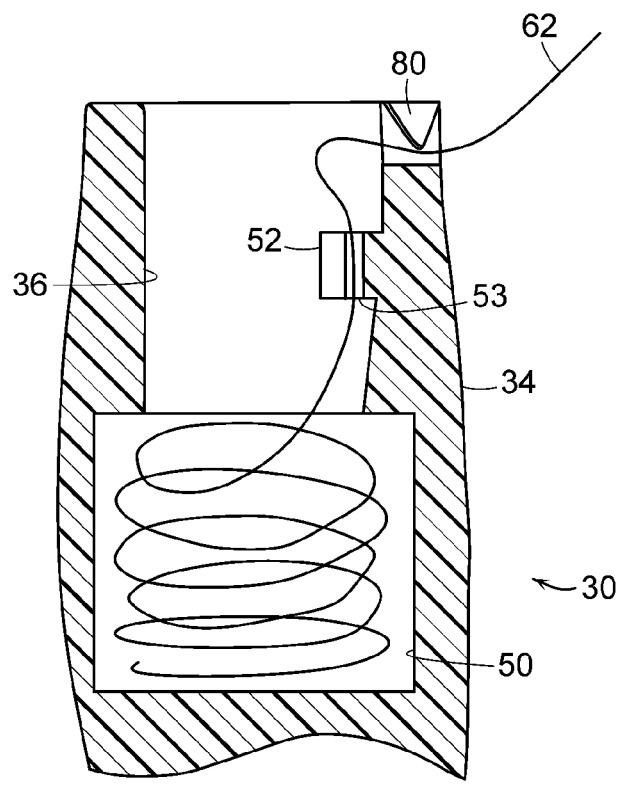
FIG. 12 is a section view of an embodiment of a distal end portion of a handle of an oral hygiene device.

Referring to FIG. 12, a limiting element 52 may be provided within cavity 50 or bore 36 to inhibit the entire strand 62, 64 from being too freely pulled from (or even entirely extracted from) the cavity. By way of non-limiting example, limiting element 52 may be a projection extending from a wall of the cavity or bore (or formed in the wall of the cavity or bore) with a hole or slot 53 formed therein. A length of floss may extend through the hole or slot. The dimensions of the hole or sidewalls of the slot may somewhat inhibit the free extension of the strand 62, 64 from the interior cavity due to friction. As an aide to floss accessibility, limiting element 52 may further inhibit the end of strand 62, 64 that is extending from handle 30 from falling or receding back into interior cavity 50. Limiting element 52 could further function as a key for orienting head 20 relative to handle 30, as discussed above.

In a further embodiment, a floss cutting element 80 may be provided on oral hygiene device 100. Floss cutting element 80 may be provided on handle 30. As shown in FIG. 12, floss cutting element may be incorporated into a wall of handle 30 that forms a portion of bore 36. A slot with a blade capable of capturing and cutting a floss strand when a user tugs the floss, as is known in the art, may be provided. Other suitable floss cutting elements will be apparent to those skilled in the art, given the benefit of this disclosure. Further, floss cutting element may be combined with the functionality of a limiting element or even an engagement element.

The supply of floss 60 may be of any type that is commonly used, including by way of non-limiting examples, multifilament floss, such as Nylon, monofilament floss, such as poly (tetrafluoroethylene) (PTFE), unwaxed floss, waxed floss, flavored floss, etc.

Oral hygiene device 100, in its entirety, may be disposable. Alternatively, head 20 or handle 30 may each, individually, be disposable and/or replaceable.

In the embodiments of FIGS. 1 through 6, tooth cleaning elements 90 are positioned on and extend outwardly from head 20. As used herein, the terms "tooth cleaning elements" and "cleaning elements" include any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements include, but are not limited to, tufts of bristles that can be formed to have a number of different shapes and sizes, and elastomeric cleaning members that can be formed to have a number of different shapes and sizes, or a combination of both tufts of bristles and elastomeric cleaning members.

Head 20 may be provided with any of a variety of oral hygiene elements. By way of non-limiting examples, head 20 may include tooth cleaning elements such as bristles or other elastomeric cleaning members, gum massaging elements, tongue cleaning elements, floss holding elements, etc.

Suitable materials for handle 30 and head 20 include, by way of non-limiting example, injection molded plastics. One or more materials may be used, including hard thermoplastics and/or elastomeric materials. Materials may be co-molded, overmolded or applied subsequently. Other suitable materials will be readily apparent to those skilled in the art, given the benefit of this disclosure.

In general, it is expected that handle 30 will be ergonomically designed for use with head 20. It is to be appreciated that the shape of the handle depicted in the illustrative drawings herein is not limiting and that other shapes for handle 30 will be suitable as will be apparent to those skilled in the art, given the benefit of this disclosure.

In light of the foregoing disclosure of the invention and description of various embodiments, those skilled in this area of technology will readily understand that various modifications and adaptations can be made without departing from the scope and spirit of the invention.

The invention claimed is:

1. A toothbrush comprising:
a head having bristles extending outwardly therefrom;
a handle configured to accommodate, at a distal end of the handle, a proximal end of the head;
a cavity provided in one of the head and the handle;
a supply of floss disposed within the cavity;
wherein one end of a strand of the supply of floss is affixed to the head and the other end of the strand of the supply of floss is affixed to the handle; and
wherein the cavity becomes accessible when the head and the handle are at least partially detached from one another along an interface of the handle and the head, the interface located at the distal end of the handle and the proximal end of the head, the proximal end of the head being narrowed relative to the distal end of the handle.

2. The toothbrush of claim 1, further comprising a bore in one of the handle or the head and a shaft on the other of the handle or the head, the shaft configured for insertion into the bore, and a seal member provided within a channel on one of the shaft or the bore.

3. The toothbrush of claim 1, wherein the head and the handle are configured to be completely detached from one another.

4. The toothbrush of claim 1, further comprising a strap connected to and extending between the handle and the head.

5. The toothbrush of claim 4, wherein the strap is detachable from one or both of the head and the handle.

6. The toothbrush of claim 1, wherein the strand of the supply of floss has a length of from approximately one-half inch to approximately 6 inches.

7. The toothbrush of claim 1, wherein the cavity is provided within the handle and the other end of the strand of the supply of floss is affixed inside the cavity.

8. The toothbrush of claim 1, further comprising a seal element between the head and the handle.

9. The toothbrush of claim 1, wherein the only opening to the cavity is provided at the interface of the head with the handle.

10. The toothbrush of claim 1, wherein one of the handle and the head includes a bore and the other of the handle and the head includes a shaft configured for slidable insertion into the bore, and wherein the bore and the shaft are configured so that relative rotation between the handle and the head is prevented.

11. The toothbrush of claim 10 wherein one of the bore and the shaft comprises a keyway and the other of the bore and the shaft comprises a key, and wherein relative rotation between the handle and the head is prevented by complementary engagement between the keyway and the key.

12. The toothbrush of claim 10 wherein the bore and the shaft comprise non-circular cross-sections, and wherein relative rotation between the handle and the head is prevented by complementary engagement between the bore and the shaft.

13. The toothbrush of claim 12 wherein one of the bore and the shaft comprises an engagement element and the other of the bore and the shaft comprises an engagement hollow, and wherein axial separation between the handle and the head is prevented by complementary engagement between the engagement element and the engagement hollow.

14. The toothbrush of claim 1 wherein the handle has a length that is greater than a length of the head.

15. A toothbrush comprising:
a head having bristles extending outwardly therefrom;
a handle configured to accommodate, at a distal end of the handle, a proximal end of the head;
a cavity provided in one of the head and the handle;
a supply of floss disposed within the cavity;
wherein the cavity becomes accessible when the head and the handle are at least partially detached from one another along an interface of the handle and the head;
wherein one of the handle and the head includes a bore and the other of the handle and the head includes a shaft configured for slidable insertion into the bore;
wherein one of the bore and the shaft comprises a keyway and the other of the bore and the shaft comprises a key, the key having a passageway extending therethrough, a portion of the supply of floss extending through the passageway to inhibit free extension of the supply of floss from the cavity; and
wherein relative rotation between the handle and the head is prevented by engagement between the keyway and the key.

16. The toothbrush of claim 15, wherein the cavity is provided within the handle and the handle further comprises an upstanding wall that extends from the cavity to the distal end of the handle, a floss cutting element incorporated into the upstanding wall at the distal end of the handle.

17. The toothbrush of claim 15 wherein the bore and the shaft comprise non-circular cross-sections, and wherein relative rotation between the handle and the head is further prevented by complementary engagement between the bore and the shaft.

18. The toothbrush of claim 17 wherein one of the bore and the shaft comprises an engagement element and the other of the bore and the shaft comprises an engagement hollow, and wherein axial separation between the handle and the head is prevented by complementary engagement between the engagement element and the engagement hollow.

19. The toothbrush of claim 15 wherein the handle has a length that is greater than a length of the head.

20. A toothbrush comprising:
a head having bristles extending outwardly therefrom;
a handle configured to accommodate, at a distal end of the handle, a proximal end of the head;
a bore in one of the handle or the head and a shaft on the other of the handle or the head, the shaft configured for insertion into the bore, the shaft having a longitudinal axis;
a projection extending outwardly from the shaft; and
wherein one end of a strand of a supply of floss is affixed to one of the head or the handle by winding the supply of floss around the shaft beneath the projection, the projection forming a hook that prevents upward axial movement of the supply of floss along the shaft.

21. The toothbrush of claim 20 wherein the other end of the supply of floss is free.

* * * * *